United States Patent
Cooper et al.

(10) Patent No.: US 9,564,073 B2
(45) Date of Patent: Feb. 7, 2017

(54) DISPLAY ANALYSIS USING SCANNED IMAGES

(71) Applicant: Amazon Technologies, Inc., Reno, NV (US)

(72) Inventors: Ted John Cooper, Sunnyvale, CA (US); Omair Abdul Rahman, Santa Clara, CA (US)

(73) Assignee: Amazon Technologies, Inc., Reno, NV (US)

( * ) Notice: Subject to any disclaimer, the term of this patent is extended or adjusted under 35 U.S.C. 154(b) by 218 days.

(21) Appl. No.: 14/483,019

(22) Filed: Sep. 10, 2014

(65) Prior Publication Data

US 2014/0376800 A1     Dec. 25, 2014

Related U.S. Application Data

(62) Division of application No. 13/663,329, filed on Oct. 29, 2012, now Pat. No. 8,867,817.

(51) Int. Cl.

| | |
|---|---|
| *G06K 9/00* | (2006.01) |
| *G06T 7/00* | (2006.01) |
| *G09G 3/00* | (2006.01) |
| *G06K 9/68* | (2006.01) |
| *G01N 21/88* | (2006.01) |
| *G01N 21/95* | (2006.01) |
| *G09G 5/02* | (2006.01) |

(52) U.S. Cl.
CPC .......... *G09G 3/006* (2013.01); *G01N 21/8851* (2013.01); *G01N 21/95* (2013.01); *G06K 9/00* (2013.01); *G06K 9/68* (2013.01); *G06T 7/001* (2013.01); *G06T 7/0004* (2013.01); *G01N 2201/105* (2013.01); *G06T 2207/10008* (2013.01); *G06T 2207/10024* (2013.01); *G06T 2207/10048* (2013.01); *G06T 2207/30121* (2013.01); *G09G 5/02* (2013.01); *G09G 2330/10* (2013.01)

(58) Field of Classification Search
None
See application file for complete search history.

(56) References Cited

U.S. PATENT DOCUMENTS

| | | | |
|---|---|---|---|
| 5,319,459 A | | 6/1994 | Mochizuki et al. |
| 5,394,481 A | | 2/1995 | Kumagai et al. |
| 5,572,444 A | | 11/1996 | Lentz et al. |
| 5,717,780 A | * | 2/1998 | Mitsumune ............. G06T 7/001 348/92 |
| 5,917,935 A | * | 6/1999 | Hawthorne ........... G02F 1/1303 348/126 |
| 5,982,946 A | | 11/1999 | Murakami |
| 6,154,561 A | * | 11/2000 | Pratt ....................... G06T 7/001 345/904 |

(Continued)

Primary Examiner — Utpal Shah
(74) Attorney, Agent, or Firm — Lowenstein Sandler LLP

(57) ABSTRACT

A method for analyzing displays is described. A processing device receives a first scanned image of a first display and determines a first characteristic of the first display by analyzing the first scanned image. The processing device also receives a second scanned image of a second display and determines a second characteristic of the second display by analyzing the second scanned image. The processing device compares the first characteristic and the second characteristic to determine a third characteristic of the second display.

17 Claims, 4 Drawing Sheets

(56) References Cited

U.S. PATENT DOCUMENTS

| | | | | |
|---|---|---|---|---|
| 7,468,611 B2 * | 12/2008 | Nguyen | ............ | G09G 3/006 |
| | | | | 324/750.22 |
| 7,812,866 B2 | 10/2010 | Sasaki | | |
| 7,859,274 B2 * | 12/2010 | Kim | ............ | G02F 1/1309 |
| | | | | 250/310 |
| 8,320,658 B2 * | 11/2012 | Tanizaki | ............ | G06T 7/0004 |
| | | | | 348/177 |
| 8,340,457 B2 * | 12/2012 | Hayakawa | ............ | G09G 3/006 |
| | | | | 382/141 |
| 8,537,144 B2 * | 9/2013 | Matthijs | ............ | G09G 3/006 |
| | | | | 345/204 |
| 2010/0278415 A1 | 11/2010 | Liege et al. | | |

\* cited by examiner

DISPLAY ANALYSIS USING SCANNED IMAGES

CROSS-REFERENCE TO RELATED APPLICATIONS

This application is a continuation of U.S. patent application Ser. No. 13/663,329, filed on Oct. 29, 2012, and incorporated by reference herein in its entirety.

BACKGROUND

A large and growing population of users enjoy entertainment through the consumption of digital media items, such as music, movies, images, electronic books and so on. Users employ various electronic devices to consume such media items. Among these electronic devices are electronic book readers, cellular telephones, personal digital assistants (PDAs), portable media players, tablet computers, netbooks and the like.

These electronic devices often include a display which can display text, images, videos or other media. Such displays may suffer from various defects that reduce a user's enjoyment of digital media consumption.

BRIEF DESCRIPTION OF THE DRAWINGS

The present invention will be understood more fully from the detailed description given below and from the accompanying drawings of various embodiments of the present invention, which, however, should not be taken to limit the present invention to the specific embodiments, but are for explanation and understanding only. Further, it should be understood that the drawings are not necessarily proportional or to scale.

DETAILED DESCRIPTION

Embodiments of a method for analyzing displays of mobile devices are described. The method may be used, for example, during a manufacturing process as part of quality control to achieve automated defect detection in displays of mobile devices. The method may include analyzing a scanned image of a display. By using a scanner to generate the image, lighting is constant and reflections and shadows are eliminated. Further, as opposed to a camera-generated image, a scanned image has improved contrast and less distortion introduced by the lens.

In one embodiment, the scanned image of a display used for analysis is generated using a commercially available flatbed scanner. Thus, the method does not introduce significant hardware costs to the analysis of displays. For example, the method may use a fixture on the commercially available flatbed scanner with the majority of the scanning area coated such that no light leakage is possible. In one embodiment, various color planes (e.g., red, green, and blue) of the display are turned on and off manually by a quality inspector or automatically by a processing device. For each color plane, a full color image on the flatbed scanner is captured. In one embodiment, the image is analyzed to determine that the color intended to be displayed lies between a maximum value (e.g., 255 for an 8-bit image) and an acceptable minimum value (e.g., 200) and that the other colors lie between a minimum value (e.g., 0) and an acceptable maximum value (e.g., 25). In one embodiment, the acceptable minimum values and acceptable maximum values are adaptively determined to account for changes in the brightness of the display in specific areas. This adaption may be propagated to other color planes to verify a consistent failure of any plane relative to the other plane's brightness levels.

The results of the analysis may be presented to a quality inspector stating that the display passed or that the display failed to meet quality control requirements. If the display fails, a picture highlighting the failed plane(s) and/or pixels involved may be presented. In one embodiment, the location and number of dead pixels may be saved as a log for later debugging reference. The log may be analyzed to determine if the dead pixels define a cluster of a particular size. This may indicate faulty construction of the various planes used in the display. On the other hand, single defective pixels which are not in a cluster may denote broken electronic wiring in the structure.

Figure 1:
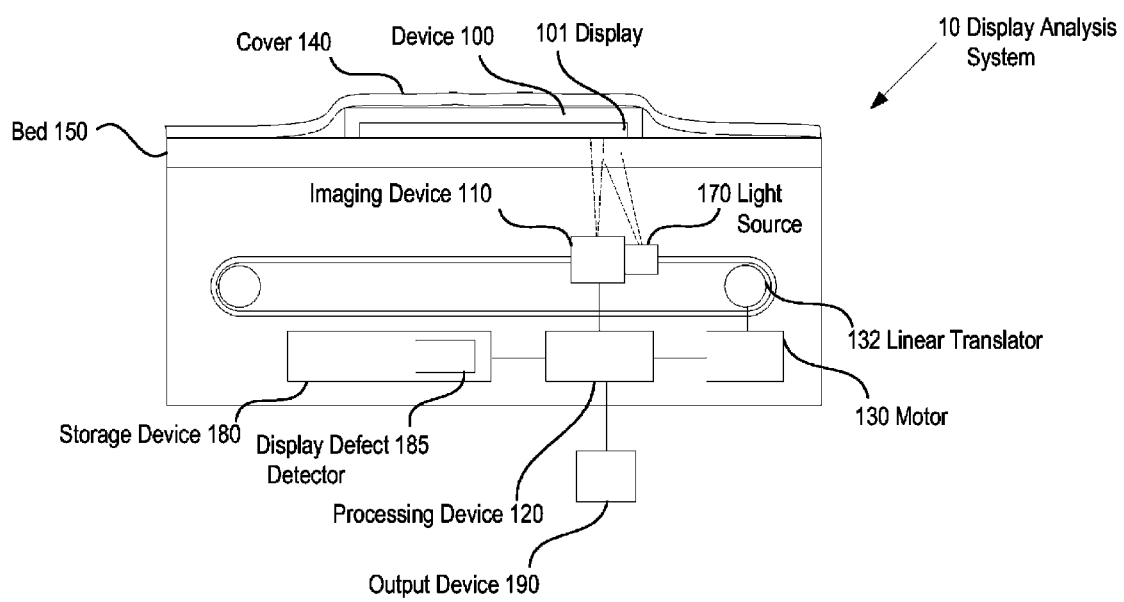
FIG. 1 illustrates a functional block diagram of a display analysis system.

FIG. 1 illustrates a functional block diagram of a display analysis system 10. The display analysis system 10 functions to analyze the display 101 of a mobile device 100 placed within or upon the system 10. The display analysis system 10 may analyze the display 101 to determine one or more characteristics of the display 101. For example, the system 10 may determine the presence or absence of a defect of the display 101. Thus, the system 10 may be beneficially used during display manufacturing as part of quality control. As another example, the system 10 may determine an average brightness, a color consistency or a maximum contrast of the display 101. Thus, the system 10 may be beneficially used during display design to measure the efficacy of various design parameters. In addition, the display analysis system 10 may determine characteristics of the display 101 other than those described above.

The mobile device 100 may be an electronic book reader, a cellular telephone, a personal digital assistant (PDAs), a portable media player, a tablet computer, a netbook or any portable, compact electronic device. The display 101 may be a liquid crystal display (LCD), an electronic paper display, or any another type of display. For example, an electronic paper display may be a bi-stable LCD display, a microelectromechanical system (MEMS) display, a cholesteric display, an electrophoretic display, or another electronic paper display. One example electronic paper display that may be used is an E (electrophoretic) Ink-brand display.

The display analysis system 10 includes an imaging device 110 configured to image a portion of display 101. The imaging device 110 is configured to generate a one-dimensional array of pixel values representing the portion of the display 101. The imaging device 110 may be configured to generate three one-dimensional arrays, each corresponding to a different color (e.g., red, green and blue), or to generate a one-dimensional array of color triplets. The imaging device 110 may include a light sensor that detects an amount of light impinging on the sensor (or upon each part of the sensor) so as to generate an image or a portion of an image, such as a one-dimensional array of pixel values. In one embodiment, the light sensor detects visible light. In another embodiment, the light sensor detects infrared or ultraviolet light. Thus, the resulting image represents this detection. In one embodiment, the imaging device 110 comprises a charge-coupled device (CCD). In another embodiment, the imaging device 110 comprises a complementary metal oxide semiconductor (CMOS) sensor. The imaging device 110 may include other light sensors. The imaging device 110 may include optics to direct light towards the light sensor. For example, the imaging device 110 may include a mirror or a lens. Because the imaging device 110 is configured to generate one-dimensional arrays of pixel values, the imaging device 110 may have only a one-dimensional lens. In another embodiment, the imaging device 110 may not include a lens.

The imaging device 110 is mechanically coupled to a motor 130 that includes a linear translator 132. The motor 130, using the linear translator 132, moves the imaging device 110 (or at least a portion thereof) along a line. In one embodiment, the motor 130 moves a light sensor of the imaging device 110. In another embodiment, the motor moves a mirror of the imaging device 110 and the light sensor is not moved by the motor 130.

The linear translator 132 may be a device which moves an object in a line. In one embodiment, the linear translator 132 comprises a reticular chain. In another embodiment, the linear translator 132 comprises a belt. In yet another embodiment, the linear translator comprises a rod. The linear translator 132 may include other components. The imaging device 110 is moved by the motor 130 in a line perpendicular to the dimension in which the pixel values of the one-dimensional array of pixel values are aligned. While being moved by the motor 130, the imaging device 110 generates multiple one-dimensional arrays of pixel values for corresponding portions of the display 101. The multiple one-dimensional arrays of pixel values may be concatenated or otherwise combined to form a two-dimensional image of the display 101.

The display analysis system 10 includes a bed 150 upon which the mobile device 100 under test is placed. The bed 150 is at least partially optically transparent. In one embodiment, the bed 150 comprises a glass window. The imaging device 110 is oriented towards the bed 150 and the display 101 of the mobile device 100 resting thereon. Similarly, the display 101 of the mobile device 100 under test is oriented towards the imaging device 110.

The display analysis system 10 may include a cover 140 that reduces or eliminates the ambient light detected by the imaging device 110. In one embodiment, the cover 140 comprises a black cloth that is draped over the bed 150. In another embodiment, the cover 140 comprises an optically opaque film. In one embodiment, the cover 140 includes a cut-out into which the device 100 is placed such that the display 101 of the mobile device 100 is visible to the imaging device 110 while the remainder of the bed is covered by the cover 140.

The display analysis system 10 may include a light source 170 configured to illuminate the portion of the display 101 imaged by the imaging device. In one embodiment, the light source 170 is moved by the motor 130 such that the light source 170 and imaging device 110 are fixed with respect to one another. In one embodiment, the light source 170 comprises a xenon light. In another embodiment, the light source 170 comprises a cold cathode fluorescent light. In another embodiment, the light source 170 comprises one or more light emitting diode (LED) linear strings. The light source 170 may comprise other light-producing components.

The display analysis system 10 includes one or more processing devices 120, such as one or more central processing units (CPUs), microcontrollers, field programmable gate arrays, or other types of processing devices. The processing device 120 may be coupled to the imaging device 110 and the motor 130. The processing device 120 may communicate with the imaging device 110 to receive image data from the imaging device 110. The processing device 120 may communicate with the motor 130 to provide instructions for moving the imaging device 110 to scan the mobile device 100. In one embodiment, the processing device is further coupled to the mobile device 100 under test. The processing device 120 may communicate with the mobile device 100 to configure the display 101 into various states as described further below.

The processing device 120 is configured to analyze the image data received from the imaging device 110 to determine one or more characteristics of the display 101. For example, the processing device 120 may determine the presence or absence of a defect of the display 101 or may determine an average brightness, a color consistency or a maximum contrast of the display 101, as will be discussed in more detail below.

The display analysis system 10 also includes a storage device 180 coupled to the processing device 120 and configured to store data. For example, the processing device 120 may store the results of its analysis of the display 101 on the storage device 180. The storage device may include any combination of volatile and/or non-volatile storage devices. The storage device 120 may also include one or more types of removable storage and/or one or more types of non-removable storage. The storage device 180 may include one or more of read-only memory (ROM), flash memory, dynamic random access memory (DRAM) such as synchronous DRAM (SDRAM)), or static random access memory (SRAM)). The storage device 180 may store an operating system, various program modules, program data and/or other software components. The storage device 120 may include a computer-readable storage medium on which is stored one or more sets of instructions embodying any one or more of the methodologies or functions described herein.

In one embodiment, the storage device 180 stores a display defect detector 185. The display defect detector 185 may be embodied, for example, as software to analyze one or more scanned images of the display 101 to detect defects in the display 101. The display defect detector 185, for example, may detect the presence or absence of stuck pixels or dead pixels in the display 101. The display defect detector 185 may also determine other characteristics of the display 101 as described in further detail below with respect to FIG. 2.

The display analysis system 10 may further include an output device 190 coupled to the processing device 120. In one embodiment, when the processing device 120 determines the presence or absence of a defect of the display 101, the processing device 120 informs the operator by outputting an indication of the determination via the output device 190. The output device 190 may include a display screen, a monitor, an alarm, a light, or any other output device.

Some of the components of the display analysis system 10 may be embodied as a flatbed scanner. For example, in one embodiment the display analysis system 10 comprises a flatbed scanner that includes the imaging device 110, motor 130, bed 150, and light source 170. The flatbed scanner may include additional or fewer components.

Figure 2:
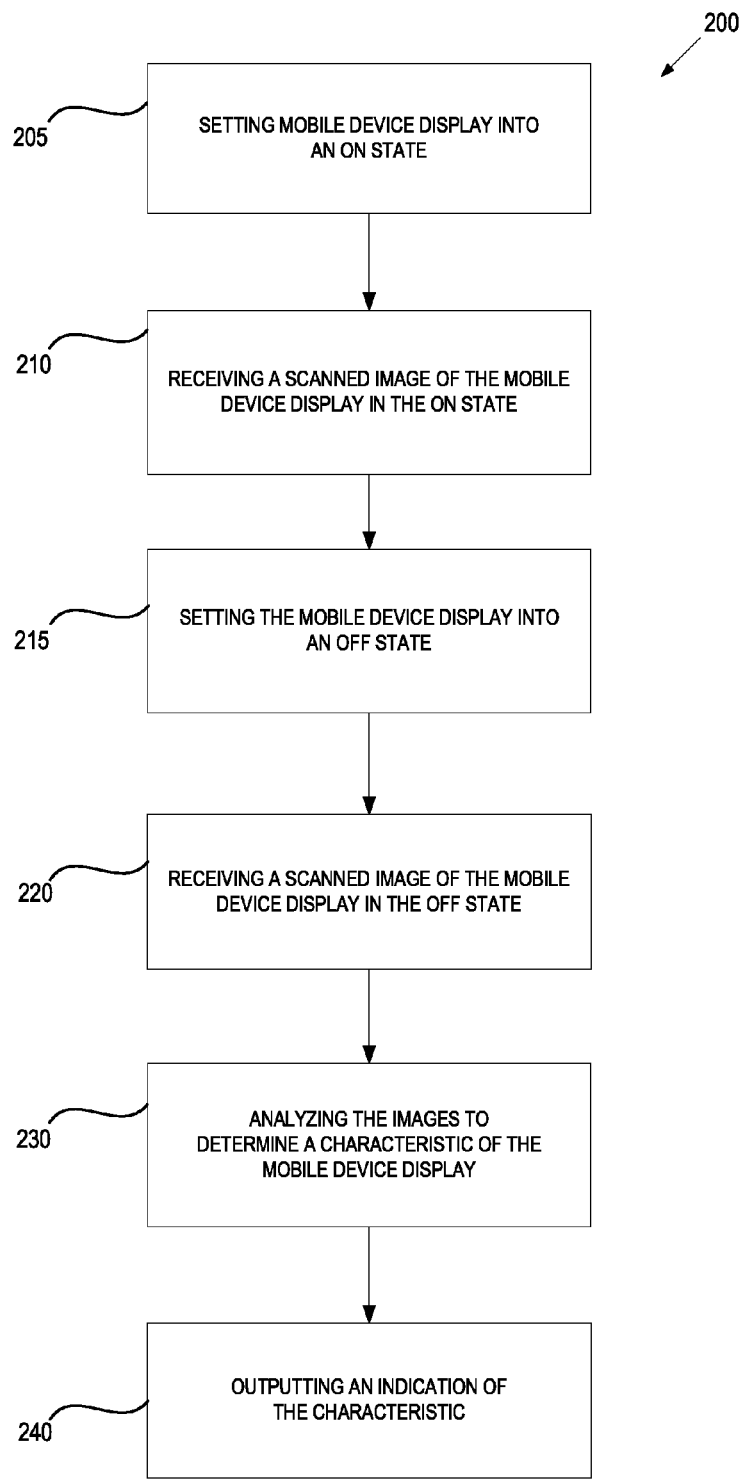
FIG. 2 illustrates a flowchart of an embodiment of a method of detecting a defect of a mobile device display using a plurality of scanned images.

FIG. 2 illustrates a flow diagram of one embodiment of a method 200 of detecting a defect of a mobile device display by analyzing a plurality of scanned images. The mobile device display may be, for example, the display 101 of FIG. 1, and the method may be performed by the display defect detector 185.

The method 200 begins, in block 205, with setting the mobile device display to an on state. In the on state, the pixels of the mobile device display are set to an on state in response to a request of a quality control inspector or automatically in response to a predefined event (e.g., when the imaging device is turned on, the mobile device display is moved to a particular position, etc.). For example, the pixels may be set such that they generate light or reflect ambient light.

In block 210, a scanned image of the mobile device display in an on state (or white state) is received. The image may be generated as the concatenation of a plurality of sequentially created one-dimensional arrays of pixel values. For example, the image may be generated by a flatbed scanner. The image may be stored as a two-dimension matrix of color triplets, each of the color triplets containing three numbers corresponding to red, green, and blue (RGB) or corresponding to hue, saturation, and brightness (HSV).

In block 215, the mobile device display is set to an off state. In the off state, the pixels of the mobile device display are set to an off state. For example, the pixels may be set such that they do not generate light or do not absorb or reflect ambient light. In block 220, a scanned image of the mobile device display in the off state (or black state) is received. In one embodiment, the scanned image is generated, using the flatbed scanner, as the concatenation of a plurality of sequentially created one-dimensional arrays of pixel values.

Although the method 200 may include the reception of two scanned images as described above with respect to blocks 210 and 220, the method 200 may also include the reception of additional scanned images corresponding to a red state, a green state, and a blue state in which, respectively, only the red pixels, green pixels, and blue pixels of the display are set to an on state. As used herein, the term "pixel" also represents elements which may otherwise be referred to as "subpixels" that correspond to specific color values of a pixel. Thus, as used herein, a single pixel may include a plurality of pixels, e.g., a single pixel may include a red pixel, a green pixel, and a blue pixel. The method 200 may also include setting the mobile device display in the red state, blue state, and green state. The method 200 may also include setting the mobile device display into other states, such as a checkered state or another patterned state. In another embodiment, the images of the mobile device display in the on state and off state are replaced completely by images of the mobile device display in the red state, blue state, green state, or other states.

In block 230, the images are analyzed to determine a characteristic of the device. In one embodiment, the determined characteristic is the presence or absence of a defect of the mobile device display. As described in detail below, a variety of different defects can be determined from analysis of the images.

In one embodiment, the images are analyzed to determine if the mobile device display includes one or more dead pixels. A dead pixel is a pixel of the display which does not transition to the on state when instructions to do so are given. For example, whereas a dead pixel should appear white in the on state, it instead appears black. The image of the mobile device display in the on state may be analyzed to determine if any pixels of the display have a brightness less than a certain minimum value (e.g. 200 on an 8-bit scale of 0 to 255). If the scanned image is in HSV format, the brightness may be determined as the V value of the portion of the image corresponding to the pixel. If the scanned image is in RGB format, the brightness of the pixel may be determined by averaging the RBG values of the portion of the image corresponding to the pixel. In another embodiment, the brightness of the pixel is determined by selecting the maximum of the RGB values of the portion of the image corresponding to the pixel or by averaging the maximum and minimum of the RGB values of the portion of the image corresponding to the pixel. If the image of the mobile device display includes brightness values below a certain minimum value, it may be determined that the device includes at least one dead pixel. In one embodiment, the number and location of dead pixels are stored in a log.

In one embodiment, the images are analyzed to determine if the mobile device display includes one or more stuck pixels. A stuck pixel is a pixel of the display which does not transition to the off state when instructions to do so are given. For example, whereas a stuck pixel should appear black in the off state, it instead appears white. The image of the mobile device display in the off state may be analyzed to determine if any pixels of the display have a brightness greater than a certain maximum value (e.g., 25 on an 8-bit scale of 0 to 255). Thus, if the image of the mobile device display includes brightness values above a certain minimum value, it may be determined that the device includes at least one stuck pixel. In one embodiment, the number and location of stuck pixels are stored in a log.

In one embodiment, scanned images with pixels of individual colors in an on state are received from the scanner. For example, a red scanned image with only red pixels in an on state, a green scanned image with only green pixels in an on state and a blue scanned image with only blue pixels in an on state may be received. These scanned images may be analyzed to determine if the mobile device display includes off-color pixels. An off-color pixel is a pixel of the display that does not display the correct color. For example, whereas an off-color pixel should appear green in the green state, the color does not appear green or appears a shade of green outside an acceptable window. The image of the mobile device display in each color state may be analyzed to determine if any pixels of the display have a hue value outside of a tolerance window. If the scanned image is in HSV format, the hue value may be determined as the H value of the portion of the image corresponding to the pixel. If the image of the mobile device display includes hue values outside a tolerance window defined for that color, it may be determined that the device includes at least one off-color pixel. If the scanned image is in RGB format, off-color pixels may also be detected by analyzing the RGB values directly. For example, if the image of the mobile device display in a particular color state (e.g., green) has a corresponding color value (e.g., G value) outside a tolerance window or below a certain value or a different color value (e.g., B value) outside a tolerance window or above a certain value, it may be determined that the display has at least one off-color pixel. In one embodiment, the number and location of off-color pixels are stored in a log.

Pixel failure can include more than a typical dead or stuck pixel, such as localized changes in brightness that indicate a specific threshold of failure but do not go so far as to indicate a full 'on' or 'off' pixel. In one embodiment, defects such as dead pixels, stuck pixels, or off-color pixels are detected using an adaptive threshold, that is, a threshold that is pixel-dependent, e.g., different for different pixels. For example, a dead pixel may be determined if a pixel set to the on state has a brightness which is significantly less than those of its neighboring pixels. For example, it may be determined that a dead pixel is present if a pixel has a brightness value less than 90% of the average of its adjacent pixels. As another example, it may be determined that a dead pixel is present if a pixel has a brightness less than 90% of the average of a 5×5 neighborhood of pixels surrounding the pixel. As a further example, it may be determined that a stuck pixel is present if a pixel has a brightness value greater than 10% of the average of its adjacent pixels or those in a neighborhood surrounding the pixel. As yet another example, it may be determined that an off-color pixel is present if a pixel has a hue value that differs by more than 5% of the average of its adjacent pixels or those in a neighborhood surrounding the pixel. Other thresholds or neighborhoods may be used.

In one embodiment, the images are analyzed to determine if the mobile device display is uniform. For example, the images may be analyzed to determine a brightness variance or a color variance and to determine that the variances are above a threshold to determine the presence of a defect or to determine that the variances are below the threshold to determine the absence of a defect. In one embodiment, the brightness variance is determined by calculating a standard deviation or the variance of the brightness values of the pixels in the on state. The variance is determined as the expected value of the square of the difference between each brightness value and the mean. The mean is determined as the average value of the brightness values. The standard deviation is determined by taking the square root of the variance. Similarly, a color variance for each color can be determined by calculating the standard deviation or the variance of the hue values of the pixels of the mobile device display in each of the color states.

In one embodiment, the images are analyzed to determine if the various color panes of the display have a consistent intensity. For example, the intensity of each color can be independently measured and compared. For example, if the images are in RGB format, the average R value of the image of the red state, the average G value of the image of the green state, and the average B value of the blue state can be compared. A defect may be detected if the values differ by more than a threshold amount. In another embodiment, the intensity of each color is compared pixel by pixel so that local variations in brightness are propagated through the color planes.

As noted above, the determined characteristic of the display may be the presence or absence of a dead pixel, a stuck pixel, or an off-color pixel. As another example, the determined characteristic of the display may be a brightness variation or a color variation. More particularly, the determined characteristic of the display may be whether or not a brightness variation or color variation exceeds a threshold. In another embodiment, the determined characteristic of the display is an average brightness or a maximum contrast.

The determined characteristic may be used during a manufacturing process to determine whether the display is defective. The determined characteristic may be used during a design process to determine the efficacy of various design parameters. The method 200 may be repeated for different displays to compare the displays. For example, the method 200 may be used to determine an average brightness for a series of displays and to track this characteristic over time. If the value is trending downwards, for example, this may indicate a defect in the manufacturing process that can be addressed before the brightness drops below acceptable levels.

The method 200 may be used to determine that a particular display is not uniform with previous displays. For example, a particular display may be determined as defective if it is more than a certain amount (e.g., 5%) less than a previously measured display or an average of previously measured displays. As another example, a particular display may be determined as defective if it has a red, green, or blue value that is more than a certain amount (e.g. 10%) different than that of a previously measured display or an average of previously measured displays.

In block 240, the results of the analysis are output. In one embodiment, the output is a message, shown on a monitor, that no defects were detected or that defects were detected. In one embodiment, if defects are detected, the nature and location of the defects are shown on the monitor. In one embodiment, the output is a message indicative whether the display has met or failed to meet quality control requirements. For example, the quality control requirements may allow no more than a particular number of defective pixels or may only allow a certain brightness or color variance.

Figure 3:
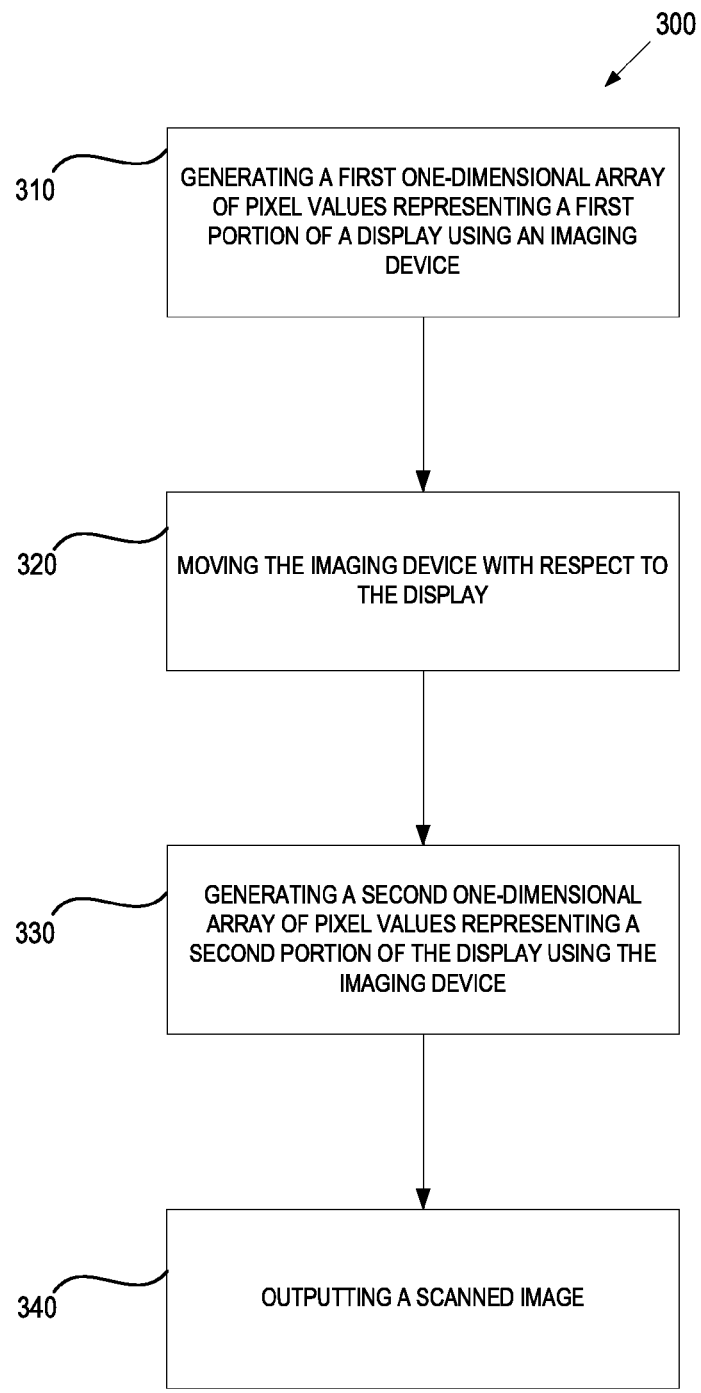
FIG. 3 illustrates a flowchart of an embodiment of a method of generating a scanned image.

FIG. 3 illustrates a flow diagram of one embodiment of a method 300 of generating a scanned image. The method 300 begins, in block 310, with the use of an imaging device to generate a one-dimensional array of pixel values representing a first portion of the display. The display may be, for example, the display 101 of FIG. 1. The imaging device may be the imaging device 110 of FIG. 1. The one-dimensional array of pixel values may include a row-array of color triplets, each of the color triplets containing three numbers corresponding to red, green, and blue (RGB) or corresponding to hue, saturation, and brightness (HSV).

In block 320, the imaging device is moved with respect to the display. The imaging device may be moved in response to initiating a scan. In particular, the imaging device may be moved as part of a scan. In one embodiment, at least a portion of the imaging device is moved and the display does not move. For example, in one embodiment, a light sensor of the imaging device is moved and the display does not move. As another example, in another embodiment a mirror of the imaging device is moved and the display does not move. In another embodiment, the display is moved and the imaging device is not moved. In another embodiment, both the display and the imaging device are moved. In one embodiment, the imaging device is linearly translated. In another embodiment, the imaging device is rotated.

In block 330, the imaging device is used to generate a one-dimensional array of pixel values representing a second portion of the display. The steps described in block 320 and 330 may be repeated until a full image of the display is generated.

In block 340, a scanned image is output. In one embodiment, the scanned image is used to determine a characteristic of the display. In one embodiment, the determined characteristic of the display is the presence or absence of a defect, such as those described above with respect to the method 200 of FIG. 2

Figure 4:
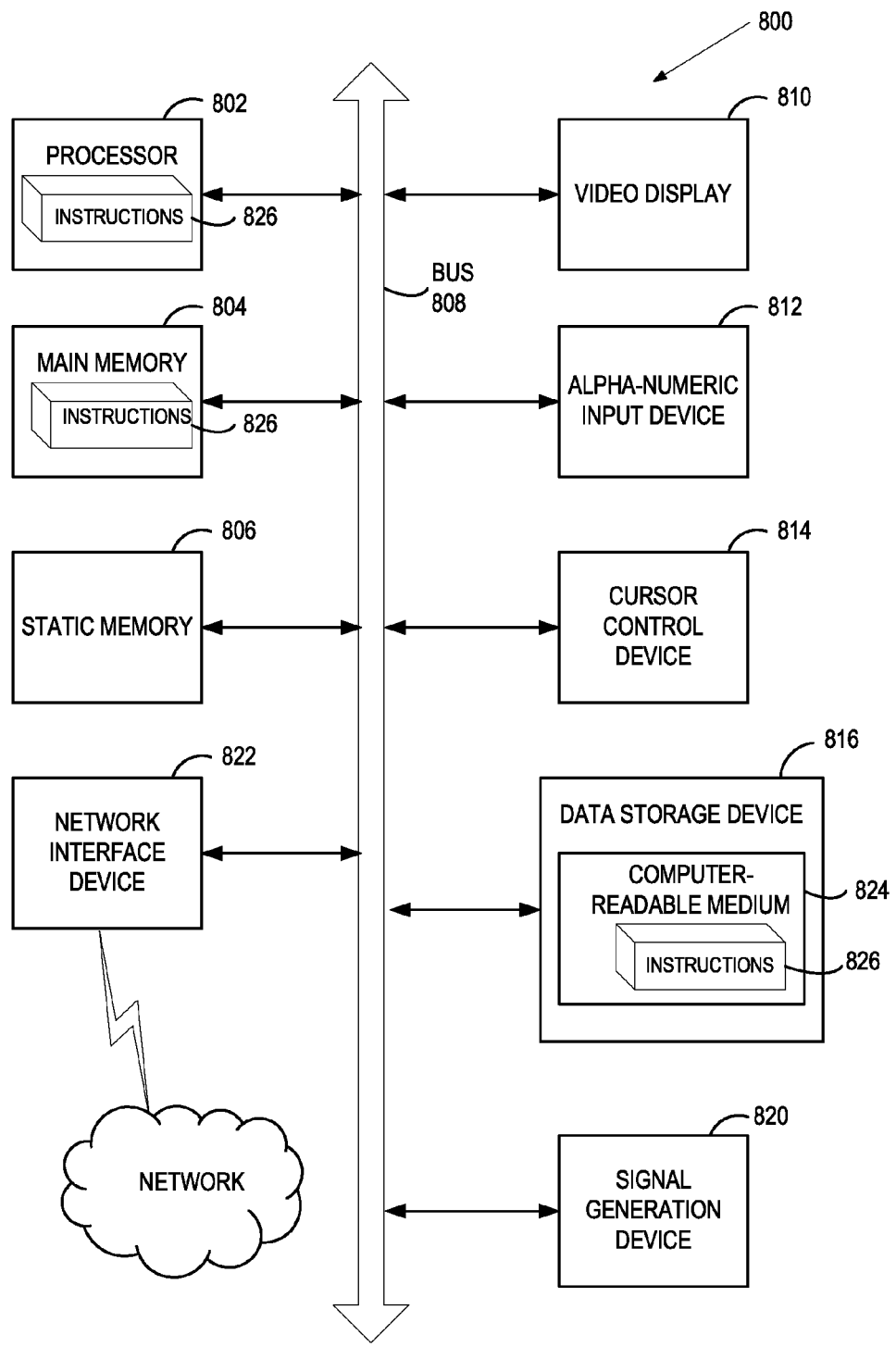
FIG. 4 illustrates a functional block diagram of an embodiment of a defect detection system.

FIG. 4 illustrates an exemplary defect detection system in the form of a computer system 800 within which a set of instructions, for causing the machine to perform any one or more of the methodologies discussed herein, may be executed. In some embodiments, the machine may be connected (e.g., networked) to other machines in a LAN, an intranet, an extranet, or the Internet. The machine may operate in the capacity of a server machine in client-server network environment. The machine may be a personal computer (PC), a set-top box (STB), a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 800 includes a processing system (processor) 802, a main memory 804 (e.g., read-only memory (ROM), flash memory, dynamic random access memory (DRAM) such as synchronous DRAM (SDRAM)), a static memory 806 (e.g., flash memory, static random access memory (SRAM)), and a data storage device 816, which communicate with each other via a bus 806.

Processor 802 represents one or more general-purpose processing devices such as a microprocessor, central processing unit, or the like. More particularly, the processor 802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 802 may also be one or more special-purpose processing devices such as an application specific integrated circuit (ASIC), a field programmable gate array (FPGA), a digital signal processor (DSP), network processor, or the like. The processor 802 is configured to execute the display defect detector 185 for performing the operations and steps discussed herein.

The computer system 800 may further include a network interface device 822. The computer system 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 820 (e.g., a speaker). The signal generation device 820 may also include a flatbed scanner that generates a signal indicative of a scanned image of mobile device display.

A drive unit 816 may include a computer-readable medium 824 on which is stored one or more sets of instructions (e.g., instructions of display defect detector 185) embodying any one or more of the methodologies or functions described herein. The instructions of the display defect detector 185 may also reside, completely or at least partially, within the main memory 804 and/or within the processor 802 during execution thereof by the computer system 800, the main memory 804 and the processor 802 also constituting computer-readable media. The instructions of the item ingestion subsystem 108 may further be transmitted or received over a network via the network interface device 822.

While the computer-readable storage medium 824 is shown in an exemplary embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present invention. The term "computer-readable storage medium" shall accordingly be taken to include, but not be limited to, solid-state memories, optical media, and magnetic media.

Embodiments of the invention also relate to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The foregoing description sets forth numerous specific details such as examples of specific systems, components, methods and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the scope of embodiments of the present invention.

In the above description, numerous details are set forth. It will be apparent, however, to one of ordinary skill in the art having the benefit of this disclosure, that embodiments of the present invention may be practiced without these specific details. In some instances, well-known structures and devices are shown in block diagram form, rather than in detail, in order to avoid obscuring the description.

It is to be understood that the above description is intended to be illustrative and not restrictive. Many other embodiments will be apparent to those of skill in the art upon reading and understanding the above description. The scope of the present invention should, therefore, be determined with reference to the appended claims, along with the full scope of equivalents to which such claims are entitled.

What is claimed is:

1. A method comprising:
   receiving, by a processing device, a first scanned image of a first display;
   determining, by the processing device, a first characteristic of the first display by analyzing the first scanned image;
   receiving, by the processing device, a second scanned image of a second display;
   determining, by the processing device, a second characteristic of the second display by analyzing the second scanned image;
   comparing, by the processing device, the first characteristic and the second characteristic to determine a third characteristic of the second display; and
   outputting an indication of the third characteristic of the second display.

2. The method of claim 1, wherein the first scanned image and the second scanned image are generated using a flatbed scanner.

3. The method of claim 1, wherein at least one of the first scanned image and the second scanned image comprises an infrared or ultraviolet image of the first display or second display.

4. The method of claim 1, wherein determining a first characteristic of the first display comprises determining an average intensity of pixels of the first display.

5. The method of claim 1, wherein the third characteristic of the second display represents at least one of presence or absence of a defect in the second display.

6. The method of claim 1, wherein the third characteristic of the second display represents at least one of an intensity variance or color variance of the second display as compared to the first display.

7. The method of claim 1, wherein the third characteristic of the second display represents an efficacy of a design parameter associated with the second display.

8. A system comprising:
a scanner to generate a first scanned image of a first display and a second scanned image of a second display, the scanner comprising: an imaging device configured to generate a one-dimensional array of pixel values corresponding to a portion of the display, and a motor configured to move the imaging device with respect to the display; and
a processing device communicatively coupled to the scanner to receive the first scanned image and the second scanned image, the processing device to determine a first characteristic of the first display by analyzing the first scanned image, determine a second characteristic of the second display by analyzing the second scanned image, and compare the first characteristic and the second characteristic to determine a third characteristic of the second display, wherein the third characteristic of the second display represents an efficacy of a design parameter associated with the second display.

9. The system of claim 8, wherein at least one of the first scanned image and the second scanned image comprises an infrared or ultraviolet image of the first display or second display.

10. The system of claim 8, wherein the first characteristic of the first display represents an average intensity of pixels of the first display.

11. The system of claim 8, wherein the third characteristic of the second display represents at least one of presence or absence of a defect in the second display.

12. The system of claim 8, wherein the third characteristic of the second display represents at least one of an intensity variance or color variance of the second display as compared to the first display.

13. The system of claim 8, further comprising a monitor to output a message representing the third characteristic of the second display.

14. A non-transitory computer-readable medium having instruction encoded thereon which, when executed by a processing device, cause the processing device to perform operations comprising:
receiving, by the processing device, a first scanned image of a first display;
determining, by the processing device, a first characteristic of the first display by analyzing the first scanned image, wherein the first display comprises an average intensity of pixels of the first display;
receiving, by the processing device, a second scanned image of a second display;
determining, by the processing device, a second characteristic of the second display by analyzing the second scanned image; and
comparing, by the processing device, the first characteristic and the second characteristic to determine a third characteristic of the second display.

15. The non-transitory computer-readable medium of claim 14, wherein the third characteristic of the second display represents at least one of presence or absence of a defect in the second display.

16. The non-transitory computer-readable medium of claim 14, wherein the third characteristic of the second display represents at least one of an intensity variance or color variance of the second display as compared to the first display.

17. The non-transitory computer-readable medium of claim 14, wherein the third characteristic of the second display represents an efficacy of a design parameter associated with the second display.

* * * * *